(12) United States Patent
Zoing Tan et al.

(10) Patent No.: US 12,213,707 B2
(45) Date of Patent: Feb. 4, 2025

(54) MEDICAL DECOUPLING INSTRUMENT

(71) Applicant: Aesculap AG, Tuttlingen (DE)

(72) Inventors: Jian Zoing Tan, Tuttlingen (DE);
Barbara Gnoth, Immendingen (DE);
Denis Ricci, Wurmlingen (DE)

(73) Assignee: Aesculap AG, Tuttlingen (DE)

( * ) Notice: Subject to any disclaimer, the term of this patent is extended or adjusted under 35 U.S.C. 154(b) by 287 days.

(21) Appl. No.: 17/771,155

(22) PCT Filed: Oct. 26, 2020

(86) PCT No.: PCT/EP2020/080073
§ 371 (c)(1),
(2) Date: Apr. 22, 2022

(87) PCT Pub. No.: WO2021/083845
PCT Pub. Date: May 6, 2021

(65) Prior Publication Data
US 2022/0401153 A1 Dec. 22, 2022

(30) Foreign Application Priority Data
Oct. 28, 2019 (DE) .................... 10 2019 129 037.6

(51) Int. Cl.
*A61B 17/70* (2006.01)
*A61B 17/00* (2006.01)
(52) U.S. Cl.
CPC ...... *A61B 17/7082* (2013.01); *A61B 17/7074* (2013.01); *A61B 2017/00477* (2013.01)

(58) Field of Classification Search
CPC ............ A61B 17/7074; A61B 17/7082; A61B 17/7076
See application file for complete search history.

(56) References Cited

U.S. PATENT DOCUMENTS 9,895,175 B2 * 2/2018 Tipping ............ A61B 17/7074
10,702,315 B2 7/2020 Lindner
(Continued)

FOREIGN PATENT DOCUMENTS

| | | |
|---|---|---|
| DE | 102016108504 A1 | 11/2017 |
| JP | 2004121643 A | 4/2004 |
| JP | 2016518214 A | 6/2016 |

OTHER PUBLICATIONS

Search Report received in German Application No. 10 2019 129 037.6 dated Jun. 8, 2020, with translation, 8 pages.
(Continued)

*Primary Examiner* — Julianna N Harvey
(74) *Attorney, Agent, or Firm* — CM Law; Christopher A. Rothe

(57) ABSTRACT

A medical decoupling instrument for decoupling a medical insertion instrument from a pedicle screw includes a shaft and a sleeve arranged around a portion of the shaft. The sleeve is configured for defined coupling to the medical insertion instrument. The shaft is rotatable relative to the sleeve, and the medical decoupling instrument is configured to bring the shaft and the sleeve autonomously and automatically into a defined starting position. A medical arrangement includes at least the medical decoupling instrument and a medical insertion instrument.

16 Claims, 3 Drawing Sheets

(56) References Cited

U.S. PATENT DOCUMENTS

| | | | |
|---|---|---|---|
| 2009/0234395 A1* | 9/2009 | Hoffman | A61B 17/7082 |
| | | | 606/104 |
| 2010/0137875 A1 | 6/2010 | Marino et al. | |
| 2013/0331892 A1 | 12/2013 | Peterson et al. | |
| 2014/0100583 A1* | 4/2014 | Butler | A61B 17/8875 |
| | | | 606/104 |
| 2014/0100616 A1* | 4/2014 | Shipp | A61B 17/7082 |
| | | | 606/86 A |
| 2014/0222081 A1* | 8/2014 | Kirschman | A61B 17/7086 |
| | | | 606/279 |
| 2014/0288567 A1* | 9/2014 | Kroll | A61B 17/7082 |
| | | | 606/104 |
| 2014/0371756 A1* | 12/2014 | Marigowda | A61B 17/7082 |
| | | | 606/104 |
| 2015/0201987 A1* | 7/2015 | Lemoine | A61B 17/8891 |
| | | | 606/104 |
| 2017/0095272 A1 | 4/2017 | Hutton et al. | |
| 2018/0263675 A1* | 9/2018 | Erramilli | A61B 17/7074 |
| 2019/0142471 A1* | 5/2019 | Lindner | A61B 17/708 |
| | | | 606/266 |
| 2021/0077155 A1 | 3/2021 | Beyer | |

OTHER PUBLICATIONS

Search Report received in International Application No. PCT/EP2020/080073 dated Mar. 29, 2021, with translation, 5 pages.
Written Opinion received in International Application No. PCT/EP2020/080073 dated Mar. 29, 2021, with translation, 10 pages.
Office Action received in Japanese Application No. 2022-524275 dated Jun. 4, 2024, with translation, 5 pages.

* cited by examiner

MEDICAL DECOUPLING INSTRUMENT

CROSS-REFERENCES TO RELATED APPLICATIONS

This application is the United States national phase entry of International Application No. PCT/EP2020/080073, filed Oct. 26, 2020, and claims priority to German Application No. 10 2019 129 037.6, filed Oct. 28, 2019. The contents of International Application No. PCT/EP2020/080073 and German Application No. 10 2019 129 037.6 are incorporated by reference herein in their entireties.

FIELD

The present invention relates to a medical decoupling instrument for decoupling a medical insertion instrument from a pedicle screw.

BACKGROUND

Pedicle screws basically serve for dorsal stabilization of the spine in cases of fractures, tumors, inflammations, deformities, and degenerative instabilities using transpedicular screw connection. Pedicle screws are placed in the pedicles of adjacent vertebrae, whereupon a stable-angle connection is created between the pedicle screws arranged axially one above the other and an axially extending, longitudinal member/rod. The pedicle screws and longitudinal members form a vertebra stabilization system.

For this purpose, a pedicle screw usually has an axial, shaft-like, externally threaded portion, which is followed on the screw head side by what is called a tulip or receiving sleeve. This constructively forms a U-shaped slotted/tunneled receiving sleeve with internal thread, wherein the two radially opposite longitudinal slots each define a slot gap of predetermined gap width. The longitudinal member/rod is inserted transversely into the longitudinal slots running parallel to each other and is fixed by a locking element, for example in the form of a grub screw, threaded nut, or setscrew, which is screwed into the internal thread.

There are two basic types of pedicle screws, i.e. monoaxial and polyaxial pedicle screws. In the case of a monoaxial pedicle screw, the externally threaded portion/shaft and the tulip/receiving sleeve are formed in one piece with each other. A polyaxial pedicle screw, on the other hand, has an externally threaded shaft manufactured as a separate component with a mostly spherical or (semi-) spherical screw head, which is embraced by the receiving sleeve/tulip so that it is relatively pivotable and is at the same time engaged in the transition region between the head and the shaft. In this way, after the externally threaded shaft has been countersunk in the pedicle passage of a vertebra, the receiving sleeve/tulip can be pivoted and/or rotated relative thereto in order to obtain a desired position and orientation essentially independent of the orientation of the shaft. The undercut prevents the receiving sleeve/tulip from being pulled off the shaft head.

Pedicle screws are inserted by a surgeon into the pedicle passage of a vertebra or respectively anchored by screwing. For this purpose, the surgeon uses, among other things, what is known as an insertion instrument, which is also referred to as a 'downtube'. The insertion instrument may have, for example, two coupling arms at its distal end, on the radially inner side of which latching structures, such as detents, are formed, which can be engaged with corresponding counter latching structures formed on the receiving sleeve/tulip of the pedicle screw.

If the surgeon wishes to decouple the insertion instrument from the pedicle screw after the pedicle screw has been screwed/anchored, a decoupling instrument is required, which is also referred to as a 'removal key'. The decoupling instrument is basically inserted into the insertion instrument and spreads the insertion instrument, in particular the coupling arms of the insertion instrument (defined elastic deformation), whereby decoupling can be realized.

In the prior art (see FIG. 1 to FIG. 4), for example, a decoupling instrument is known that can be inserted into an insertion instrument. FIG. 4 shows, for example, an upper portion of the insertion instrument in which the decoupling instrument is inserted.

The decoupling instrument known from the prior art (see in particular FIGS. 1 to 3) basically has a hollow cylindrical/sleeve-like component with a proximal handle portion. A cylindrical rod is housed in the hollow cylindrical/sleeve-like component, which has an engagement element at its distal end, which is intended to form-fittingly engage with a pedicle screw (see in particular lower portion in FIG. 2). An engagement pin is connected/attached to the proximal end of the cylindrical rod, which is received in a motion link (elongated hole) provided in the hollow cylindrical/sleeve-like component. When the cylindrical rod is form-fittingly engaged with the pedicle screw, the engagement pin allows the hollow cylindrical/sleeve-like component to rotate through approximately 90°. The motion link or elongated hole extends in the circumferential direction of the hollow cylindrical/sleeve-like component. An oval engagement portion is provided at the distal end of the hollow cylindrical/sleeve-like component (see in particular the upper portion in FIG. 2). If the hollow-cylindrical/sleeve-like component is rotated by about 90° from its starting position/zero position, the oval engagement portion of the decoupling instrument can decouple the insertion instrument, in particular it can spread the coupling arms of the insertion instrument. Basically, the decoupling instrument is usable for both coupling and decoupling of pedicle screws.

The prior art, which can be seen in FIGS. 1 to 4, basically has the disadvantage that the hollow cylindrical/sleeve-like component and the cylindrical rod have to be manually oriented to each other before the decoupling instrument is inserted into the insertion instrument. Furthermore, the form fit at the distal end between the pedicle screw and the decoupling instrument may make decoupling more difficult.

SUMMARY

Against this background, the object of the present invention is to avoid or at least reduce the disadvantages of the prior art. In particular, a medical decoupling instrument for decoupling a medical insertion instrument from a pedicle screw is to be provided, which is couplable to the medical insertion instrument in a simple manner and provides secure decoupling (in particular, elastically deforms the medical insertion instrument in a defined manner).

In the following, the terms 'proximal' and 'distal' are used such that 'proximal' means closer to the user/surgeon and 'distal' means further away from the user/surgeon.

The invention relates firstly to a medical decoupling instrument for decoupling a medical insertion instrument from a pedicle screw, in particular by spreading the medical insertion instrument open, comprising: a shaft/rod and a sleeve, which is arranged around an (in particular cylindrical) portion of the shaft/rod, said sleeve being designed for defined, in particular twist-proof, coupling to the medical insertion instrument, wherein the shaft/rod (for decoupling the medical insertion instrument from the pedicle screw) is rotatable with respect to the sleeve, and wherein the medical decoupling instrument is designed to move the shaft/rod and the sleeve self-actingly and automatically into a defined starting position/initial position/zero position.

The medical decoupling instrument according to the invention thus provides a defined zero position/starting position and preferably does not require manual orienting of the shaft and the sleeve. In other words, the shaft and the sleeve of the medical decoupling instrument according to the invention are automatically oriented to each other for insertion into the medical insertion instrument.

In an advantageous manner, the medical decoupling instrument also has a spring, in particular a helical spring/compression spring, which is arranged between a support surface, which is provided on the shaft, and the sleeve and is designed to move the shaft and the sleeve into the defined starting position/zero position via its spring force. In particular, the sleeve has a contact surface for the spring at its distal end.

It is advantageous if the shaft has a pin-shaped/peg-shaped projection at the portion around which the sleeve is arranged, the sleeve has a motion link/slotted link/elongated hole, and the peg-shaped projection of the shaft is received/arranged in the motion link of the sleeve such that the motion link defines a range of rotation/rotatability (angular range) of the shaft with respect to the sleeve.

Preferably, the motion link runs obliquely, i.e. extends both in the circumferential direction and in the axial direction of the sleeve, such that a first end of the motion link is arranged closer to a distal end of the sleeve than a second end of the motion link.

It is of particular advantage if, in the defined starting position, the peg-shaped projection of the shaft is pressed against the first end of the motion link by the spring. In other words, the spring preferably applies a compressive force to the sleeve in such a way that the peg-shaped projection/pin/peg of the shaft is located in the original position/starting position/zero position at the first end of the motion link.

Advantageously, the motion link of the sleeve allows rotating the shaft by about/approximately 90°. In other words, the elongated hole/motion link extends from the first end to the second end in the circumferential direction by about/approximately 90°.

A preferred configuration example is characterized in that the motion link has a depression/notch/trough (in the axial direction towards the distal end of the sleeve) at its second end such that the peg-shaped projection of the rod can be pressed into the depression via the spring. This allows tactile feedback to be provided to a user/operator when the medical insertion instrument is decoupled from the pedicle screw.

It is practical if the sleeve for defined coupling to the medical insertion instrument has pin-shaped/peg-shaped projections, which in particular are diametrically opposite and extend radially outward.

The peg-shaped projections are preferably designed in such a way that they can be engaged with the medical insertion instrument in such a way that the sleeve is/will be held in the medical insertion instrument in a twist-proof manner in the circumferential direction.

Furthermore, it is advantageous if the shaft has a distal engagement portion that is cylindrical with a non-circular cross-section or oval-cylindrical in shape, and in particular is designed to be engaged with/to spread open the medical insertion instrument for torque transmission.

Preferably, a portion of the shaft has a push piece that is designed to generate/apply a compressive force radially outward, in particular to press against the medical insertion instrument. In particular, the push piece is formed or designed in such a way that it can exert a push force radially outward against the medical insertion instrument so that unintentional slipping of the medical decoupling instrument is prevented.

Advantageously, the shaft has a proximal handle portion which is substantially cylindrical in shape with a round/circular or non-circular cross-section. Preferably, the proximal handle portion is fluted or has a plurality of elongated recesses/depressions extending in the axial direction, which are evenly spaced/distributed, in particular in the circumferential direction, for improved gripping (and twisting) of the shaft by a user/surgeon.

Preferably, the proximal handle portion, which is provided at a proximal end of the shaft, is axially followed by a first cylindrical portion. The first cylindrical portion of the shaft is in particular the portion of the shaft around which the hollow cylindrical sleeve is arranged, and thus the portion of the shaft which has the peg-shaped/cylindrical projection extending radially outward. The first cylindrical portion of the shaft preferably has a round/circular cross-section. The peg-shaped projection of the shaft arranged on the first cylindrical portion is preferably received in the motion link of the sleeve.

It is advantageous if the first cylindrical portion of the shaft is followed in the axial direction by a second cylindrical portion of the shaft. The second cylindrical portion has in particular a round/circular cross section. Preferably, a diameter of the second cylindrical portion is larger than a diameter of the first cylindrical portion. Advantageously, the support surface for the spring is provided/formed at a proximal end of the second cylindrical portion. The push piece is preferably provided on the second cylindrical portion of the shaft.

It is practical if the second cylindrical portion is followed in the axial direction by a third cylindrical portion, which in particular has a round/circular cross-section and whose diameter is preferably smaller than the diameter of the second cylindrical portion. This portion does not necessarily have to be round, as long as the diameter/the largest width is at no point larger than the diameter of the second cylindrical portion.

In an advantageous manner, the third cylindrical portion is followed in the axial direction by the distal engagement portion, which is provided/arranged at a distal end of the shaft.

Furthermore, the invention relates to a medical assembly comprising at least the medical decoupling instrument described above and a medical insertion instrument.

The medical decoupling instrument is preferably designed to decouple the medical insertion instrument from the pedicle screw.

In an advantageous manner, decoupling is realized in that the medical decoupling instrument is designed to decouple the medical insertion instrument, in particular two diametrically opposite coupling arms of the insertion instrument extending parallel in the axial direction from a pedicle screw.

Preferably, the coupling arms of the insertion instrument each have a detent/latching structure at their distal ends that is engageable with a counter detent/latching structure formed on a receiving sleeve/tulip of a polyaxial or monoaxial pedicle screw.

It is practical if the non-circular, distal engagement portion of the medical decoupling instrument is designed to be engaged with the coupling arms of the medical insertion instrument by twisting the shaft, in particular to disengage the coupling arms from the pedicle screw.

It is furthermore advantageous if the peg-shaped projections of the sleeve are received in the medical insertion instrument in a twist-proof manner. For this purpose, the medical insertion instrument preferably has, at its proximal end, two diametrically opposite V-shaped or U-shaped recesses extending in the axial direction, which receive the peg-shaped projections of the sleeve and hold them in a twist-proof manner.

In other words, the invention relates to a (medical) decoupling instrument ('removal key') comprising a shaft, a sleeve, and a (compression) spring mechanism.

The shaft has a pin/peg, the sleeve has a motion link/elongated hole, and the pin/peg of the shaft is received in the motion link/elongated hole of the sleeve in such a way that the sleeve and shaft can be rotated relative to each other.

The shaft has a non-circular shape at its distal end via which a (medical) insertion instrument ('downtube') can be spread for decoupling the insertion instrument from a pedicle screw.

In addition, the shaft contains a push piece or engagement mechanism, respectively, which holds the decoupling instrument in the insertion instrument.

The spring mechanism is arranged between the shaft and the sleeve in such a way that it ensures that the sleeve is always/by itself/self-actingly/automatically in a zero position/defined starting position, so that insertion of the decoupling instrument into the insertion instrument can take place without prior manual turning/orienting.

The motion link of the sleeve allows the shaft to be rotated at a predefined angle, preferably by about 90° clockwise, and can provide tactile feedback for uncoupling/spreading the insertion instrument via a small depression provided at one end of the motion link. However, this depression is not absolutely necessary for the function of the motion link.

Unintentional slipping of the decoupling instrument out of the insertion instrument is prevented by the push piece or the engagement mechanism, the depression at the motion link as well as the contact between the decoupling instrument and the insertion instrument at the distal end.

For decoupling the two instruments (decoupling instrument and insertion instrument), the decoupling instrument (the shaft of it) can be turned back, preferably by 90° counterclockwise (supported by the spring force), so that the sleeve is again in the zero position/defined starting position for the next application.

Thus, a decoupling instrument is provided, which provides a defined zero position and automatic orienting, which does not require a form closure between itself and the implant/pedicle screw, and which preferably further provides tactile feedback for decoupling. Defined spreading of the insertion instrument is ensured by the motion link and the instrument orientation (orientation of shaft and sleeve) caused by the (compression) spring.

BRIEF DESCRIPTION OF THE DRAWING FIGURES

The invention is further explained below with the aid of figures. The following is shown:

DETAILED DESCRIPTION

The figures are merely schematic in nature and serve solely to aid understanding of the invention. Identical elements are marked with the same reference signs.

Figure 1:
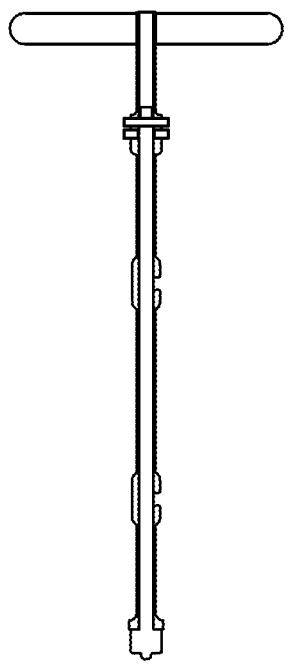
FIG. 1 shows a sectional view of a decoupling instrument known from the prior art.
Figure 2:
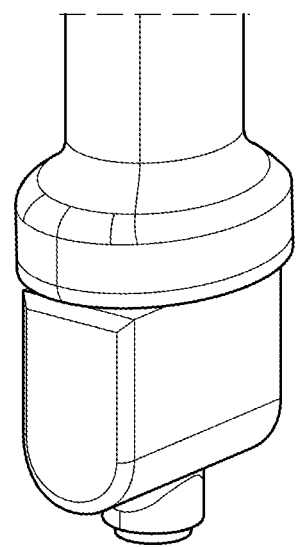
FIG. 2 shows an isometric detail view of a lower region of the decoupling instrument of FIG. 1.
Figure 3:
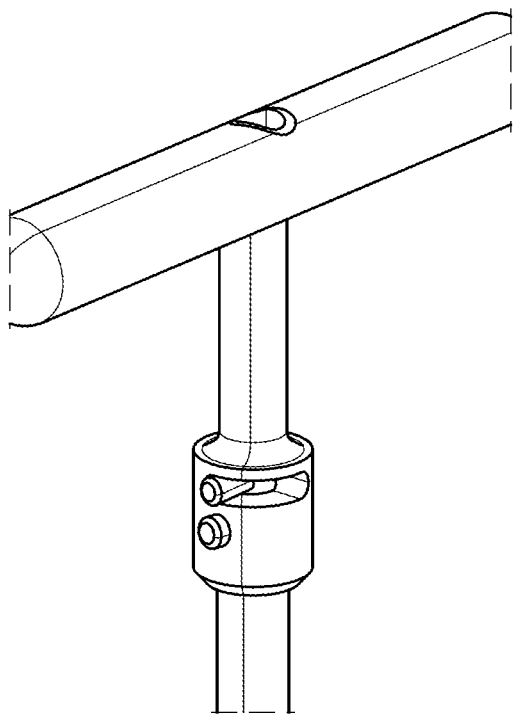
FIG. 3 shows an isometric detail view of an upper region of the decoupling instrument of FIG. 1.
Figure 4:
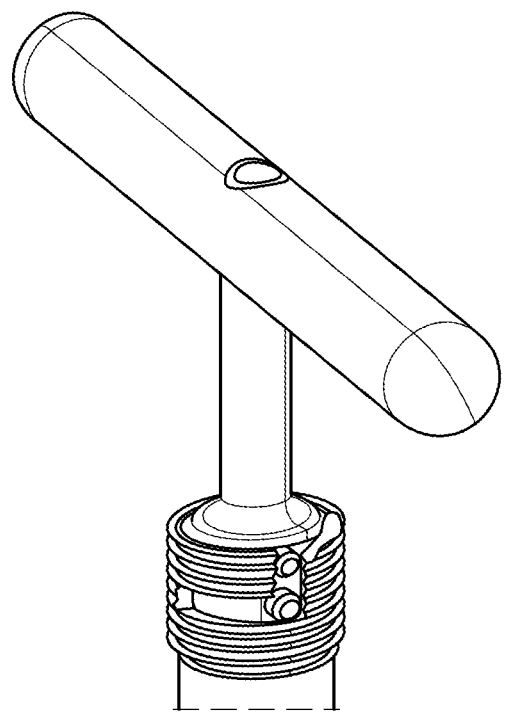
FIG. 4 shows an isometric view of the decoupling instrument of FIG. 1 inserted into an insertion instrument.
Figure 5:
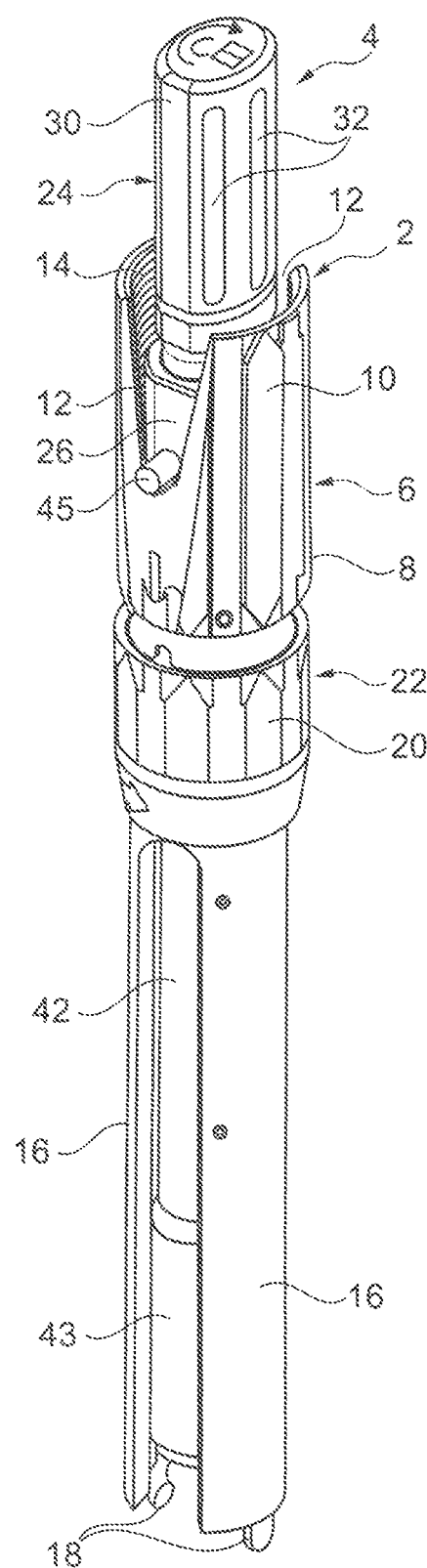
FIG. 5 shows an isometric view of the medical assembly according to the invention comprising the decoupling instrument according to the invention and an insertion instrument.

FIG. 5 shows a medical assembly 2, which comprises (among other things) a medical decoupling instrument 4 and a medical insertion instrument 6.

The insertion instrument 6 has a main body 8. This forms an upper receiving portion 10, among other things for the decoupling instrument 4. In the area of the upper receiving portion 10, the insertion instrument 6 has two V-shaped or U-shaped recesses 12 extending in the axial direction, which are designed to receive corresponding engagement structures provided on the decoupling instrument 4. In addition, the insertion instrument 6 has, in the region of the upper receiving portion 10, an internally (inner) threaded portion 14, which is designed to receive, in particular for screwing in, a different instrument (not shown) of the medical assembly 2. For example, the internally threaded portion 14 may house what is known as an insert pusher or insert presser, which serves to fix polyaxiality in the case of a polyaxial pedicle screw (by pressing on an 'insert').

Two diametrically opposite coupling arms 16 extending parallel in the axial direction follow the upper receiving portion 10 of the main body 8. At their distal ends, the coupling arms 16 have latching structures, in particular detents 18, which can basically be engaged with counter latching structures formed on a receiving sleeve/tulip of a polyaxial or monoaxial pedicle screw (not shown). The insertion instrument 6 further comprises a locking sleeve 20, which is arranged in a transition region 22 between the upper receiving portion 10 and the coupling arms 16 around the main body 8.

The insertion instrument 6 is basically designed to receive a pedicle screw, in particular a receiving sleeve/tulip of the pedicle screw, at its detents 18. In a first release position of the locking sleeve 20, the coupling arms 16 have a suitable elasticity/flexibility to receive the pedicle screw, in particular the counter latching structures of the pedicle screw, via their detents 18. By rotating the locking sleeve 20 from the first release position to a second locking position, the main body 8 is pulled axially upwards with respect to the locking sleeve 20. This fixes the coupling arms 16 by the locking sleeve 20 so that the pedicle screw is held firmly and securely by the insertion instrument 6.

If a surgeon/user wants to decouple the insertion instrument 6 from the pedicle screw after the pedicle screw has been screwed/anchored, he/she has to move the locking sleeve 20 from the second locking position to the first release position again (by twisting the locking sleeve 20). The surgeon/user also inserts the decoupling instrument 4 into the insertion instrument 6. With the aid of the decoupling instrument, the coupling arms 16 of the insertion instrument 6 can be spread/pressed radially outward, thus decoupling the pedicle screw from the insertion instrument 6.

Figure 6:
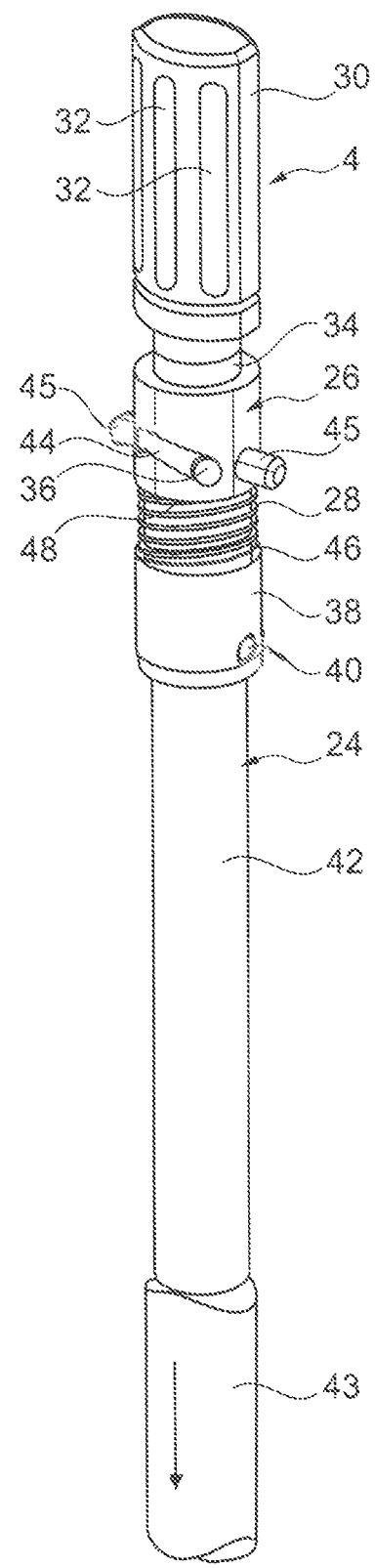
FIG. 6 shows an isometric view of the decoupling instrument according to the invention.
Figure 7:
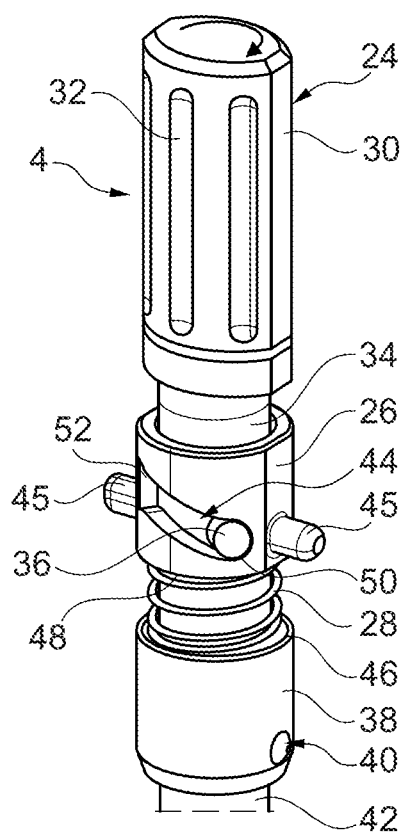
FIG. 7 shows a first isometric detail view of the decoupling instrument of FIG. 5.
Figure 8:
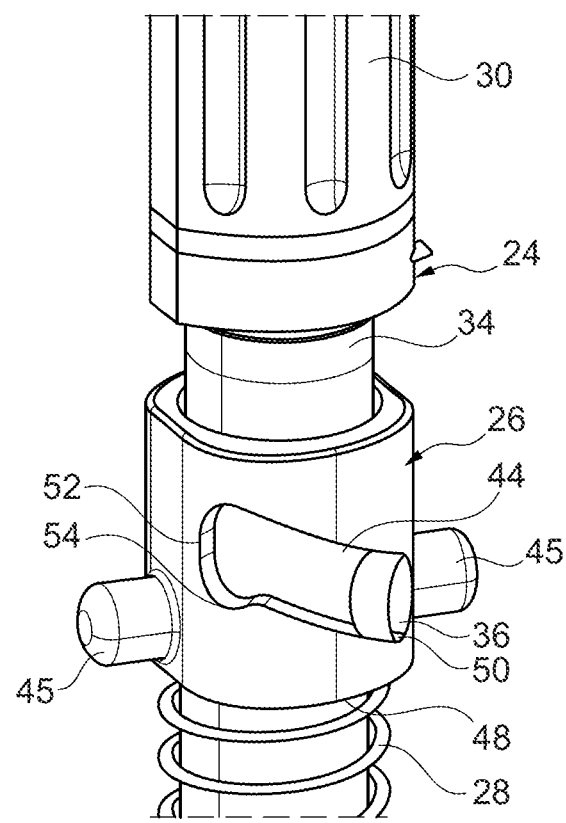
FIG. 8 shows a second isometric detail view of the decoupling instrument of FIG. 5.

The medical decoupling instrument 4 according to the invention is shown in more detail in FIG. 6, FIG. 7, and FIG. 8.

The decoupling instrument 4 basically has a shaft/rod 24, a sleeve 26, and a spring 28.

The shaft 24 has a proximal handle portion 30 at its proximal end. In the preferred example shown, the proximal handle portion 30 is oval-cylindrical in shape (cylindrical shape with an oval cross-section) and has a plurality of elongated recesses 32 extending in the axial direction and being evenly spaced/distributed in the circumferential direction, which serve to improve gripping of the shaft 24 by a user/surgeon.

A first cylindrical portion 34 with a round/circular cross-section follows the proximal handle portion 30 in the axial direction of the shaft 24. The first cylindrical portion 34 has a peg-shaped projection 36 extending radially outward.

The first cylindrical portion 34 is followed in the axial direction of the shaft 24 by a second cylindrical portion 38 with a round/circular cross-section. The second cylindrical portion 38 has a larger diameter than the first cylindrical portion 34. A push piece or engagement mechanism 40 is provided/arranged on the second cylindrical portion 38. The push piece 40 generates a compressive force radially outward and can thus press against the insertion instrument 6, so that unintentional slipping of the decoupling instrument 4 is prevented. Unintentional slipping of the decoupling instrument 4 can also be prevented by a different engagement mechanism.

The second cylindrical portion 38 is followed in the axial direction of the shaft 24 by a third cylindrical portion 42 with a preferably round/circular cross-section. The third cylindrical portion 42 has an equal or smaller diameter than the second cylindrical portion 38.

The third cylindrical portion 42 is followed in the axial direction of the shaft 24 by a distal engagement portion 43, which forms the distal end of the shaft 24. The distal engagement portion 43 is cylindrical with a non-circular cross-section.

The sleeve 26 of the decoupling instrument 4 is basically hollow cylindrical in shape and is arranged around the first cylindrical portion 34 of the shaft 24. The sleeve 26 has a motion link/elongated hole 44 in which the peg-shaped projection 36 provided on the shaft 24 is received or guided. The motion link 44 defines a range of rotation of the shaft 24 with respect to the sleeve 26. In particular, the motion link 44 of the sleeve 26 allows approximately 90° rotation of the shaft 24. The sleeve 26 has two peg-shaped projections 45 which are diametrically opposite each other and extend radially outward. The peg-shaped projections 45 of the sleeve 26 are provided to be received in the V-shaped or U-shaped recesses 12 of the insertion instrument 6, so that the sleeve 26 is/will be held in the insertion instrument 6 in a twist-proof manner.

The spring 28 is a coil spring or a compression spring and is disposed between a support surface 46 (for the spring 28), which is formed at a proximal end of the second cylindrical portion 38 of the shaft 24, and a contact surface 48 (for the spring 28), which is formed at a distal end of the sleeve 26.

The motion link 44 of the sleeve 26 extends obliquely, i.e., extends both in the circumferential direction and in the axial direction of the sleeve 26. This means that a first end 50 of the motion link 44 is arranged closer to a distal end of the sleeve 26 than a second end 52 of the motion link 44. The shape of the motion link 44, which is particularly apparent from FIG. 7 or FIG. 8, may also be present/formed in a mirrored manner (embodiment for left-handed users).

The spring 28 applies a compressive force to the sleeve 26 and pushes the sleeve 26 axially upward. As a result, the peg-shaped projection 36 of the shaft 24 is automatically or self-actingly pressed against the first end 50 of the motion link 44. When the peg-shaped projection 36 of the shaft 24 is at the first end 50 of the motion link/elongated hole 44, this represents a defined starting position/zero position/original position. In this defined starting position, the sleeve 26 and the shaft 24 are arranged with respect to each other such that when the peg-like projections 45 of the sleeve 26 are received in the V-shaped recesses 12 of the insertion instrument 6 and held in a twist-proof manner, the non-circular distal engagement portion 43 of the shaft 24 is arranged with respect to the coupling arms 16 of the insertion instrument 6 such that the coupling arms 16 are not spread. In other words, the shaft/rod 24 and the sleeve 26 of the decoupling instrument 4 are automatically oriented with respect to each other for inserting/positioning into the insertion instrument 6.

When the decoupling instrument 4 is inserted into the insertion instrument 6, the sleeve 26 (the peg-shaped projections 45 of the sleeve 26) is held in the V-shaped or U-shaped recesses 12 of the insertion instrument 6 in a twist-proof manner. A user/surgeon can now rotate the shaft 24 with respect to the sleeve 26 by turning the proximal handle portion 30 clockwise by about 90° until the peg-shaped projection 36 of the shaft 24 is located at the second end 52 of the motion link/elongated hole 44. In this position, the oval-shaped, distal engagement portion 43 of the shaft 24 spreads the coupling arms 16 of the insertion instrument 6 open, thereby decoupling the insertion instrument 6 from the pedicle screw.

As shown in particular in FIG. 8, the motion link/elongated hole 44 may have a depression/notch/trough 54 at its second end 52. However, it is also conceivable that the depression 54 is not provided. When the peg-shaped projection 36 of the shaft 24 slips or falls into or is received in the depression 54 at the second end 52 of the motion link 44, that is, in particular is pressed into the depression 54 by the spring 28, tactile feedback is provided to a user/surgeon indicating to the user/surgeon that the insertion instrument 6 is decoupled from the pedicle screw.

In this position, unintentional slipping of the decoupling instrument 4 is prevented by the push piece 40, which presses against the insertion instrument 6 from the inside, the depression 54 on the motion link 44, and the contact between the decoupling instrument 4 and the insertion instrument 6 at its distal end.

For decoupling the two instruments (decoupling instrument 4 and insertion instrument 6), the decoupling instrument 4 can be turned back 90° counterclockwise (supported by the spring force) so that the sleeve 26 is again in the zero position/starting position for the next application.

The invention claimed is:

1. A medical decoupling instrument for decoupling a medical insertion instrument from a pedicle screw, comprising: a shaft and a sleeve which is arranged around a portion of the shaft, said sleeve being configured for defined coupling to the medical insertion instrument, wherein the shaft is rotatable about a longitudinal axis of the shaft with respect to the sleeve, and wherein the medical decoupling instrument is configured to move the shaft and the sleeve self-actingly and automatically into a defined initial position, the medical decoupling instrument further comprising a spring which is arranged between a support surface, which is provided on the shaft, and the sleeve and is arranged to move the shaft and the sleeve into the defined initial position via its spring force, wherein the shaft has a peg-shaped projection at the portion around which the sleeve is arranged, the sleeve has a motion link, and the peg-shaped projection of the shaft is received in the motion link of the sleeve such that the motion link defines a range of rotation of the shaft with respect to the sleeve, wherein the motion link runs obliquely and thus extends both in a circumferential direction and an axial direction of the sleeve, such that a first end of the motion link is arranged closer to a distal end of the sleeve than a second end of the motion link in the axial direction and that the first end of the motion link is distanced from the second end of the motion link in the circumferential direction, and wherein the medical decoupling instrument is configured such that by rotating the shaft by an angle defined about the longitudinal axis of the shaft by the first end of the motion link and the second end of the motion link the peg-shaped projection of the shaft moves along the motion link from the first end of the motion link to the second end of the motion link.

2. The medical decoupling instrument according to claim 1, wherein in the defined initial position the peg-shaped projection of the shaft is pressed against the first end of the motion link by the spring.

3. The medical decoupling instrument according to claim 1, wherein the motion link has a depression at its second end such that the peg-shaped projection of the shaft can be pressed into the depression via the spring.

4. The medical decoupling instrument according to claim 1, wherein the sleeve has peg-shaped projections for defined coupling to the medical insertion instrument.

5. The medical decoupling instrument according to claim 1, wherein the shaft has a distal engagement portion that is cylindrically shaped with a non-circular cross-section.

6. The medical decoupling instrument according to claim 1, wherein a portion of the shaft has a push piece or an engagement mechanism that is configured to apply a push force radially outward.

7. The medical decoupling instrument according to claim 1, wherein the motion link allows a 90° rotation of the shaft about the longitudinal axis of the shaft with respect to the sleeve in the circumferential direction such that the peg-shaped projection moves 90° in the circumferential direction from the first end of the motion link to the second end of the motion link.

8. A medical assembly comprising at least the medical decoupling instrument according to claim 1 and a medical insertion instrument.

9. The medical assembly according to claim 8, wherein the medical insertion instrument comprises V-shaped or U-shaped recesses, the sleeve of the medical decoupling instrument comprises radially projecting peg-shaped projections, and the radially projecting peg-shaped projections lie on distal ends of the V-shaped or U-shaped recesses such that they are received and held in the V-shaped or U-shaped recesses in a twist-proof manner.

10. The medical assembly according to claim 8, wherein the medical insertion instrument comprises coupling arms extending parallel in an axial direction and having latching structures at their distal ends, and the shaft of the medical decoupling instrument comprises a distal engagement portion which with rotation of the shaft about the longitudinal axis of the shaft spreads the coupling arms of the medical insertion instrument.

11. A medical decoupling instrument for decoupling a medical insertion instrument from a pedicle screw, the medical decoupling instrument comprising:
   a shaft having a support surface;
   a sleeve which is arranged around a portion of the shaft, wherein the sleeve is slidable along and rotatable about the shaft through a predefined limited non-zero range of linear and angular motion; and
   a spring which is arranged between the support surface of the shaft and the sleeve; wherein
   the sleeve has projections provided for defined coupling to the medical insertion instrument; and
   the spring is provided to slide and rotate the shaft relative to the sleeve through the predefined limited non-zero range of linear and angular motion, self-actingly and automatically into a defined initial position along the predefined limited non-zero range of linear and angular motion;
   wherein the shaft has a peg-shaped projection at said portion of the shaft, the sleeve has a motion link, and the peg-shaped projection is received in the motion link such that the motion link defines the predefined limited non-zero range of linear and angular motion;
   wherein the motion link runs obliquely and thus extends both in a circumferential direction and an axial direction of the sleeve, such that a first end of the motion link is arranged closer to a distal end of the sleeve than a second end of the motion link in the axial direction and that the first end of the motion link is distanced from the second end of the motion link in the circumferential direction; and
   wherein the medical decoupling instrument is configured such that, by rotating the shaft about a longitudinal axis of the shaft with respect to the sleeve by an angle about the longitudinal axis of the shaft defined by the first end of the motion link and the second end of the motion link, the peg-shaped projection of the shaft moves along the motion link from the first end of the motion link to the second end of the motion link.

12. The medical decoupling instrument according to claim 11, wherein the peg-shaped projection of the shaft, in the defined initial position, is pressed against the first end of the motion link by the spring.

13. The medical decoupling instrument according to claim 11, wherein the motion link has a depression at its second end such that the peg-shaped projection is pressable into the depression via the spring.

14. The medical decoupling instrument according to claim 11, wherein the motion link defines a 90° predefined non-zero limited range of angular motion of the shaft with respect to the sleeve in a circumferential direction such that the peg-shaped projection moves 90° in the circumferential direction from the first end of the motion link to the second end of the motion link.

15. The medical decoupling instrument according to claim 11, wherein the shaft has a distal engagement portion that is cylindrically shaped with a non-circular cross-section.

16. The medical decoupling instrument according to claim 11, wherein a portion of the shaft has a push piece or an engagement mechanism that is configured to apply a push force radially outward.

* * * * *